United States Patent [19]

Hikosaka

[11] Patent Number: 5,602,249

[45] Date of Patent: Feb. 11, 1997

[54] PROCESS FOR THE PRODUCTION OF COPPER PHTHALOCYANINE PIGMENT

[75] Inventor: Michichika Hikosaka, Tokyo, Japan

[73] Assignee: Toyo Ink Manufacturing Co., Ltd., Tokyo, Japan

[21] Appl. No.: 412,887

[22] Filed: Mar. 29, 1995

[30] Foreign Application Priority Data

Apr. 1, 1994 [JP] Japan .................................. 6-064951

[51] Int. Cl.$^6$ .......................... C09B 67/50; C09B 47/04
[52] U.S. Cl. .......................... 540/144; 540/122; 540/139; 540/142
[58] Field of Search ............................ 540/122, 139, 540/142, 144

[56] References Cited

U.S. PATENT DOCUMENTS

| | | | |
|---|---|---|---|
| 2,647,127 | 7/1953 | Brouillard | 260/314.5 |
| 2,668,171 | 2/1954 | Compton | 260/314.5 |
| 5,393,339 | 2/1995 | Gerson et al. | 540/144 |
| 5,449,774 | 9/1995 | Lambie et al. | 540/144 |

FOREIGN PATENT DOCUMENTS

| | | |
|---|---|---|
| 0436311 | 7/1991 | European Pat. Off. . |
| 2162227 | 7/1973 | France . |
| 2646211 | 4/1977 | Germany . |
| 1368385 | 9/1974 | United Kingdom . |
| 15524878 | 9/1979 | United Kingdom . |
| 2101659 | 5/1987 | United Kingdom . |

OTHER PUBLICATIONS

Dainichi Color, Patent Abstracts of Japan, vol. 011 No. 315 (C-451) 14 Oct. 1987 JP-A-62 101 659 12 May 1987.

*Primary Examiner*—Mukund J. Shah
*Assistant Examiner*—Pavanaram K. Sripada
*Attorney, Agent, or Firm*—Wenderoth, Lind & Ponack

[57] ABSTRACT

A process for the production of a copper phthalocyanine by a urea method, which enables the production of a highly pure copper phthalocyanine and/or its derivative by a uniform reaction, i.e., is free from problems of an insufficient mixing, nonuniformity in heat transfer and adhesion of the reaction mixture to a reactor wall, the process comprising heating a raw material mixture containing a phthalic acid, a nitrogen source, a copper compound and a catalyst in an inert solvent, the process being carried out in the presence of a surfactant which enables the raw material mixture and a reaction product to be dispersed in the inert solvent while the raw materials are being reacted and which can be removed or deactivated by hydrolysis with an acid or an alkali at a step of purifying the reaction product or forming the reaction product into a pigment after the reaction.

15 Claims, No Drawings

PROCESS FOR THE PRODUCTION OF COPPER PHTHALOCYANINE PIGMENT

FIELD OF THE INVENTION

The present invention relates to a process for the production of a highly pure phthalocyanine and/or a highly pure derivative thereof useful in the fields of pigments and dyes, at high yields.

PRIOR ART OF THE INVENTION

For the production of copper phthalocyanines, conventionally, there is industrially most widely employed a method in which a phthalic anhydride and/or its derivative, a copper compound and urea are heated in an inert solvent in the presence of a catalyst. This method is known as a urea method or Wyler method.

The above urea method is industrially widely used at present. In the course of the reaction, however, none of the mixture of raw materials, a reaction intermediate arid a product is brought in to a completely dissolved state. That is, the reaction proceeds in a heterogeneous state from beginning to end. Further, at the step at which the reaction intermediate is formed, the viscosity of the reaction system increases to cause an insufficient mixing, nonuniformity in heat transfer and adhesion of the reaction mixture to a reactor wall. As a result, not only the operation for the reaction is hindered, but also the purity and yield of the product are decreased.

For overcoming the above defects, there have been proposed some methods in which, for example, a solvent having a high dissolving power is used to improve the stirring of the reaction system, or a solvent is used in an amount as small as about 2 times the amount of phthalic acid to have a good effect on the reaction yield. However, the problem of the former method is that it is not sufficient to produce a good effect and that there is some limitation to the selection of a solvent which can be easily handled. In the latter method, the reaction system shows an increase in viscosity since the amount of the solvent is small, and there is therefore a defect in that it is required to increase the stirring power and the strength of the stirring apparatus.

JP-A-5-5866 discloses that the viscosity can be decreased by adding an anionic surfactant to the reaction system and that the a mount of the solvent therefore can be decreased. This method can undoubtedly have a great effect on the improvement of the reaction system. However, there is another problem in that an anionic surfactant contained in a pigment decrease s the interfacial tension between an offset printing ink and water to cause some problems such as the scumming of a printing plate, etc. It is very difficult to completely remove the anionic surfactant added to the reaction system in the subsequent steps of purification and pigment formation. Although it is clear that the above method is advantageous in view of the reaction step, it cannot solve all the problems when the suitability for use for the production of a pigment is taken into consideration. It is therefore strongly desired to develop a process for producing a highly pure copper phthalocyanine at high yields by improving the stare of the reaction system without impairing the suitability for use and the economic performance.

SUMMARY OF THE INVENTION

It is an object of the present invention to provide a process for the production of a copper phthalocyanine by a urea method, which enables the production of a copper phthalocyanine and/or its derivative by a uniform reaction.

It is another object of the present invention to provide a process for the production of a copper phthalocyanine by a urea method, which is free from problems such as an insufficient mixing, nonuniformity in heat transfer and adhesion of the reaction mixture to a reactor wall, all caused by an increase in the viscosity of the reaction system when a reaction intermediate is formed.

It is further another object of the present invention to provide a process for the production of a copper phthalocyanine by a urea method, which enables the production of a highly pure copper phthalocyanine and/or derivative thereof suitable for use as a printing ink, at high yields with high economic performance.

According to the present invention, there is provided a process for the production of a copper phthalocyanine by heating a raw material mixture containing a phthalic acid, a nitrogen source, a copper compound and a catalyst in an inert solvent, the process being carried out in the presence of a surfactant which enables the raw material mixture and a reaction product to be dispersed in the inert solvent while the raw materials are being reacted and which can be removed or deactivated by hydrolysis with an acid or an alkali at a step of purifying the reaction product or forming the reaction product into a pigment after the reaction.

DETAILED DESCRIPTION OF THE INVENTION

The present inventor has made diligent studies to achieve the above object, and as a result, has found the following. When a certain surfactant decomposable with an acid or an alkali is added during the production of phthalocyanine by a urea method, the reaction system shows a decreased viscosity and an improved uniformity, and the reaction proceeds smoothly. Further, the surfactant added to the reaction system can be removed or deactivated with an acid or an alkali in the subsequent step of purifying the reaction product or forming it into a pigment. Therefore, there can be produced copper phthalocyanine which has a high purity and has n problem in the suitability for use.

The above surfactant used in the present invention has the following formula (1), $$(R^1—B)_k—A(X_m, Y_n) \tag{1}$$

wherein $R^1$ is a saturated or unsaturated aliphatic hydrocarbon having 1 to 20 carbon atoms, B is —COO—, —OCO— or —CO—, A is a direct bond, a saturated or unsaturated hydrocarbon or a sorbitan residue, X is hydrogen, hydroxyl or —COO$^-$M$^+$, Y is hydrogen, hydroxyl, —(OCH$_2$CH$_2$)$_p$—Z— or —D—SO$_3^-$M$^+$, k is 1 or 2, each of m and n is 0 to 3, p is 1 to 20, Z is —OH or —(OCOR$^2$), D is —O— or a direct bond, $R^2$ is a saturated or unsaturated hydrocarbon having 1 to 20 carbon atoms, and M is K or Na, provided that when B is —OCO— or —C—, B forms —COO— together with A or Y.

Any compounds which satisfy the above formula (1) may be used alone or in combination.

The phthalic acid or derivative thereof used in the present invention includes phthalic acid, alkali metal salt of phthalic acid, ammonium salt of phthalic acid, organic amine salt of phthalic acid, phthalic anhydride, phthalimide, phthalic acid diamide, phthalodinitrile, 1,3-diaminoisoindoline, and the same compounds as these except that 1 to 4 halogen atoms are substituted on their benzene ring. These compounds may be used alone or in combination.

The nitrogen source such as urea is generally used in an amount of at least 3 mol per mole of the phthalic acid and/or its derivative. Substituted urea such as biuret may be used. Further, when a phthalic acid containing no nitrogen such as phthalic acid or phthalic anhydride is used as a raw material, part of urea may be replaced with ammonia or an ammonium compound in the first imidation reaction.

The copper source used in the present invention is typically copper chloride, while it may be selected from copper salts such as a metal copper powder, copper oxide, copper sulfate and copper acetate and complexes of copper salts such as copper chloride and any one of ammonia, urea and an amine.

The catalyst used in the present invention is generally ammonium molybdate, while it may be selected from molybdenum (VI) oxide and molybdic acid. The catalyst is used in an amount, as a molybdenum content, of 0.001 to 0.02 part by weight based on the phthalic acid.

The inert solvent used in the present invention can be selected from hose solvents which are conventionally used for the production of copper phthalocyanine, such as nitrobenzene, trichlorobenzene, chloronaphthalene, alkylbenzenes, alkylnaphthalenes and kerosenes. The amount of the inert solvent is 1 to 5 times, preferably 1.5 to 2.5 times, as large as the amount of the phthalic acid. When the amount of the inert solvent is larger than the above upper limit, the stir ring can be carried out easily, while the yield of a copper phthalocyanine tends to decrease. When this amount is less than the above lower limit, the viscosity of the reaction system increases and it is difficult to stir the reaction system.

The surfactant characteristic of the present invention is a compound which is deactivated under proper hydrolysis conditions where the surfactant alone is decomposed but the reaction product (copper phthalocyanine) is not decomposed, in the step of purifying the reaction product or forming the reaction product into a pigment. The surfactant is selected from an anionic surfactant, a nonionic surfactant, a cationic surfactant and an amphoteric surfactant, all of which have structures hydrolyzable with an acid or an alkali. Particularly preferred are compounds of the formula (1) which have at least one ester group such as an aliphatic ester group or a sorbitan ester group.

Examples of the surfactant include the following.

(1) Acyl aliphatic polyhydric alcohol sulfuric acid ester salts:

Compounds of the formula (1) in which B is —COO—, A is an aliphatic residue, Y is —D—$SO_3M^+$ (D is —O—) and each of k, m and n is 1.

(2) Sulfoethanol fatty acid ester salts

Compounds of the formula (1) in which B is —COO—, A is a saturated aliphatic residue, Y is —D—$SO_3M^+$ (D is a direct bond), k is 1, n is 1 and m is zero (0).

(3) Alkylsulfoacetic acid salts

Compounds of the formula (1) in which B is —OCO—, A is a saturated aliphatic group, Y is —D—$SO_3M^+$ (D is a direct bond), n is 1 and m is zero (0).

(4) Dialkylsulfosuccinic acid salts

Compounds of the formula (1) in which $R^1$ is an alkyl group having 6 to 18 carbon atoms, B is —OCO—, A is an ethane residue such as —$CH_2$—CH=, Y is —$SO_3Na$, k is 2, m is 0, and n is 1.

(5) Monoalkylsulfosuccinic acid salts

Compounds of the formula (1) in which $R^1$ is an alkyl group having 6 to 18 carbon atoms, B is —OCO—, A is an ethylene group, X is —$COO^-Na^+$, Y is —$SO_3^-Na^+$, k i s 1, m is 1, and n is 1.

(6) Polyoxyethylene monofatty acid esters

Compounds of the formula (1) in which $R^1$ is an alkyl group having 5 to 17 carbon atoms, B is —CO—, A is a direct bond, Y is —($OCH_2$—$CH_2)_p$—OH, k is 1, m is 0, n is 1, and p is 1 to 20.

(7) Polyoxy ethylene propylene glycol fatty acid esters

Compounds of the formula (1) in which $R^1$ is an alkyl group having 5 to 17 carbon atoms, B is —COO—, A is a propane residue, Y is —($OCH_2CH_{2p}$—OH, and k is 1, m is 0 (zero), n is 1 and p is 1 to 20.

(8) Polyoxy ethylene sorbitan monofatty acid esters

Compounds of the formula (1) in which $R^1$ is an alkyl group having 5 to 17 carbon atoms, B is —COO—, A is a sorbitan residue, X is —OH, Y is —($OCH_2CH_2)_p$—OH, k is 1, m is 0 to 3, n is 3 to 0, and p is 1 to 20.

The amount of the above surfactant per 1 part by weight of the phthalic acid is 0.005 to 0.15 part by weight.

The process for the production of a copper phthalocyanine, provided by the present invention, can be carried out under known production conditions (temperature, time and pressure) and known post-treatment conditions (solvent removal and purification). For example, the process is carried out approximately at a temperature of 160° to 220° C. for 2 to 8 h ours under a pressure of atmospheric pressure to 5 kg/cm². When the surfactant specified in the present invention is used, the reaction system retains a stable dispersed stare, and the reaction proceeds smoothly, all through the reaction as compared with the case where the surfactant is absent. After the reaction, the solvent is removed from the reaction product by a conventional method, and then the surfactant is removed by hydrolysis by heating the reaction product in an environment of an acid or an alkali, whereby a highly pure copper phthalocyanine having excellent suitability for use can be obtained. The hydrolysis is carried out in the presence of a solution of 1 to 5% by weight of a n acid or an alkali in water at a temperature of 70° to 100° C. for 0.5 to several hours. The amount of the above acid or alkali solution is 5 to 100 parts by weight per 1 part by weight of the copper phthalocyanine.

EXAMPLES

The present invention will be explained more in detail hereinafter with reference to Examples, in which "%" stands for "% by weight" and "part" stands for "part by weight".

EXAMPLE 1

59.2 Parts of phthalic anhydride, 78 parts of urea, 9.7 parts of cuprous chloride and 0.592 part of ammonium molybdate we re allowed to react in 108 parts of Hisol P (alkylbenzene solvent, supplied by Nippon Petrochemical Co., Ltd.) in the presence of 2.37 parts of a surfactant of the formula (1) in which $R^1$ was octyl, B was —OCO—, A was —$CH_2$—CH=, Y was —$SO_3^-Na^-$, k was 2, m was 0 and n was 1, under atmospheric pressure at a temperature between 190° and 200° C. for 4 hours. During the reaction, the system retained a well-mixed state, and the reaction proceeded smoothly. After the reaction, the solvent was removed by evaporation under reduced pressure, and 10 parts, per 1 part of the remainder, of an aqueous solution containing 1% of sodium hydroxide was added to the remainder. The mixture was heated at 90° C. for 1 hour, filtered, washed with water and dried to give 56.0 part of a crude copper phthalocyanine (Crude-1, purity 98.2%, yield 95.5%). Crude-1 was formed into a pigment by a conventional method to give a β-form copper phthalocyanine pigment (Pigment-1).

5.0 Grams of Pigment-1 was wetted with 5 ml of methanol, and then dispersed in 200 ml of pure water, and the dispersion was stirred at 80° C. for 60 minutes. Then, the dispersion was cooled to room temperature, pure water was added to the dispersion so that the mixture had a weight of 300 g, and the mixture was filtered. The resultant filtrate was measured for a surface tension to show 68.7 mN/m. This value is about the same as a value of surface tension shown in Comparative Example 2. That is, it was shown that when the synthesis of copper phthalocyanine was carried out in the presence of the above surfactant, the surfactant was free from decreasing the surface tension or having an adverse influence on the emulsifiability of an offset ink.

EXAMPLE 2

59.2 Parts of phthalic anhydride, 90 parts of urea, 9.9 parts of cuprous chloride and 0.179 part of ammonium molybdate were allowed to react in 118 parts of kerosene in the presence of 3.55 parts of a surfactant of the formula (1) in which $R^1$ was $C_{11}$ linear saturated alkyl, B was —COO—, A was a sorbitan residue, X was —OH, k was 1, m was 3 and n was 0, under a pressure of 2.5 kg/cm² in the same manner as in Example 1, and the reaction mixture was post-treated in the same manner as in Example 1 to give 55.8 parts of a crude copper phthalocyanine (Crude-2, purity 98.0%, yield 95.0%) The state of the reaction system was as good as that in Example 1.

Crude-2 was formed into a pigment by a conventional method t give a β-form copper phthalocyanine pigment (Pigment-2).

Pigment-2 was extracted with water in the same manner as in Example 1, and the resultant filtrate was measured for a surface tension to show 68.0 mN/m. This value shows that when the synthesis of copper phthalocyanine was carried out in the presence of the above surfactant, the surfactant was free from decreasing the surface tension or having an adverse influence on the emulsifiability of an offset ink.

EXAMPLE 3

58.8 Parts of phthalimide, 66 parts of urea, 10.1 parts of cuprous chloride and 0.237 part of ammonium molybdate were allowed to react in 136 parts of Hisol P in the presence of 1.76 parts of a surfactant of the formula (1) in which $R^1$ was $C_{11}$ alkyl, B was —CO—, A was a direct bond, Y was —(OC$_2$H$_4$)$_4$—OH, k was 1, m was 0 and n was 1, in the same manner as in Example 1, and the reaction mixture was post-treated in the same manner as in Example 1 to give 55.4 parts of a crude copper phthalocyanine (Crude-3, purity 97.6%, yield 94.0%). The state of the reaction system was as good as that in Example 1.

Crude-3 was formed into a pigment by a conventional method to give a β-form copper phthalocyanine pigment (Pigment-3).

Pigment-3 was extracted with water in the same manner as in Example 1, and the resultant filtrate was measured for a surface tension to show 68.0 mN/m. This value shows that when the synthesis of copper phthalocyanine was carried out in the presence of the above surfactant, the surfactant was free from decreasing the surface tension or having an adverse influence on the emulsifiability of an offset ink.

EXAMPLE 4

50.1 Parts of phthalic anhydride, 14.3 parts of sodium monochlorophthalate, 108 parts of urea, 9.9 parts of cuprous chloride and 0.414 part of ammonium molybdate were allowed to react in 149 parts of kerosene in the presence of 2.58 parts of a surfactant of the formula (1) in which $R^1$ was $C_{17}$ alkyl, B was —COO—, A was a propane residue, X was —OH, Y was —OSO$_3^-$Na$^+$ and each of k, m and n was 1, in the same manner as in Example 1, and the reaction mixture was post-treated in the same manner as in Example 1 to give 55.8 parts of a crude low-chloro copper phthalocyanine (Crude-4, purity 97.0%, yield 91.0%). The state of the reaction system was as good as that in Example 1.

Crude-4 was formed into a pigment by an acid paste method to give an α-form low-chloro copper phthalocyanine pigment (Pigment-4). Pigment 4 was excellent in dispersibility and an ink containing Pigment 4 was also excellent in resistance to wetting water.

Comparative Example 1

59.2 Parts of phthalic anhydride, 90 parts of urea, 9.9 parts of cuprous chloride and 0.178 part of ammonium molybdate were allowed to react in 112 parts of Hisol P in the presence of 3.55 parts of sodium dodecylbenzenesulfonate (additive) in the same manner as in Example 1, and the reaction mixture was post-treated in the same manner as in Example 1 to give 56.8 parts of a crude copper phthalocyanine (Crude-5, purity 97.0%, yield 93.0%). The state of the reaction system was as good as that in Example 1.

Crude-5 was formed into a pigment by a conventional method to give a β-form copper phthalocyanine pigment (Pigment-5).

Pigment-5 w as extracted with water in the same manner as in Example 1, and the resultant filtrate was measured for surface tension to show 37.5 mN/m. This value shows that the additive greatly decreased the surface tension of the pigment and impaired the emulsifiability of the pigment in an off set ink.

Further, Pigment-5 was repeatedly washed with a 1% sodium hydroxide aqueous solution, and then extracted with water. The filtrate was measured for a surface tension to show 45.3 mN/m. This value is insufficient, and shows that the additive was not fully removed.

Comparative Example 2

59.2 Parts of phthalic anhydride, 90 parts of urea, 9.9 parts of cuprous chloride and 0.178 part of ammonium molybdate we followed to react in 112 parts of Hisol P in the absence of a surfactant in the same manner as in Example 1, and the reaction mixture was post-treated in the same manner as in Example 1 to give 55.3 parts of a crude copper phthalocyanine (Crude-6, purity 96.9%, yield 93.0%). The reaction system showed no excellent state, since a gummy intermediate product and the solvent were separated, and the intermediate product adhered to a reactor wall.

Crude-6 was formed into a pigment by a conventional method to give a β-form copper phthalocyanine pigment (Pigment-6). Pigment-6 was extracted with water in the same manner as in Example 1, and the resultant filtrate was measured for a surface tension to show 69.2 mN/m. This value shows that when no surfactant is incorporated, a filtrate has a sufficiently high surface tension. That is, this value can be used as an index for excellence in emulsifiability.

In the process for the production of copper phthalocyanine by a urea method, provided by the present invention, the viscosity of the reaction system is low during the reaction so that the uniformity of the reaction system is high, and the reaction therefore proceeds smoothly. As a result, highly pure copper phthalocyanine can be obtained at high yields. After the reaction, the surfactant added for the reaction can be removed or deactivated with an acid or an alkali, and the resultant copper phthalocyanine pigment is free from causing the problems in the suitability for use, such as a decrease in the interfacial tension between an offset printing ink and water, or soiling on printing plate at the time of printing.

What is claimed is:

1. A process for the production of a copper phthalocyanine by heating a phthalic acid, a nitrogen source, a copper compound and a catalyst in an inert solvent in the presence of a surfactant, which surfactant can be removed or deactivated by hydrolysis with an acid or an alkali when purifying the reaction product or forming the reaction product into a pigment after the reaction, said surfactant having formula (1):

$$(R^1-B)_k-A(X_m, Y_n) \quad (1)$$

wherein $R^1$ is alkyl or alkenyl having 1 to 20 carbon atoms; B is —COO—, or —CO—; k is an integer of 1 or 2; A is a direct bond, a saturated or unsaturated hydrocarbon, or a sorbitan residue; X is hydrogen, hydroxyl or —COO$^-$M$^+$; m is an integer of 0 to 3; Y is hydrogen, hydroxyl, or —(OCH$_2$CH$_2$)$_p$—Z or —D—SO$_3^-$M$^+$, where p is an integer of 1 to 20, Z is —OH or —(OCOR$^2$) with R$^2$ being a saturated or unsaturated hydrocarbon having 1 to 20 carbon atoms, D is —O— or a direct bond; M is K or Na; and n is an integer of 0 to 3, provided that when B is —CO—, B forms —COO— together with A or Y.

2. A process according to claim 1, wherein the nitrogen source is added in an amount of at least 3 mol per mole of the phthalic acid.

3. A process according to claim 1, wherein the catalyst is added in an amount of 0.001 to 0.02 part by weight per 1 part by weight of the phthalic acid.

4. A process according to claim 1, wherein the inert solvent is added in an amount which is 1 to 5 times by weight of the phthalic acid.

5. A process according to claim 1, wherein the surfactant is added in an amount of 0.005 to 0.15 part by weight per 1 part by weight of the phthalic acid.

6. A process according to claim 1, wherein the surfactant is selected from compounds of the formula (1) wherein $R^1$ is an alkyl group having 5 to 17 carbon atoms, B is —COO—, A is a sorbitan residue, X is —OH, Y is —(OCH$_2$CH$_2$)$_p$—OH, k is 1, m is 0 to 3, n is 3 to 0, m+n is 3 and p is 1 to 20.

7. A process according to claim 1, wherein the surfactant is selected from compounds of the formula (1) wherein $R^1$ is an alkyl group having 5 to 17 carbon atoms, B is —COO—, A is a propane residue, X is —OH, Y is —SO$_3$Na, and each of k, m and n is 1.

8. A process according to claim 1, wherein the wherein $R^1$ is an alkyl group having 5 to 17 carbon atoms, B is —CO—, A is a direct bond, Y is —(OCH$_2$—CH$_2$)$_p$—OH, k is 1, m is 0, n is 1, and p is 1 to 20.

9. A process according to claim 1, wherein the hydrolysis with an acid or an alkali is carried out using a solution of 1 to 5% by weight of an acid or an alkali in water, the amount of the solution being 5 to 100 parts by weight per 1 part by weight of the copper phthalocyanine.

10. A process according to claim 1, wherein the hydrolysis with an acid or an alkali is carried out at a temperature in the range of from 70° to 100° C.

11. The method of claim 1, wherein the phthalic acid is selected from the group consisting of phthalic acid, an alkali metal salt of phthalic acid, an ammonium salt of phthalic acid, an organic amine salt of phthalic acid, phthalic anhydride, phthalimide, phthalic acid diamide, phthalodinitrile, 1,3-diaminoisoindoline, and derivatives thereof for which 1 to 4 halogen atoms are substituted on a benzene ring therein.

12. The process of claim 1, wherein the nitrogen source is selected from the group consisting of urea, biuret, ammonia, and an ammonium compound.

13. The process of claim 1, wherein the copper source is selected from the group consisting of copper chloride, copper metal, copper oxide, copper sulfate, copper acetate, and complexes of copper salts with any one of ammonia, urea, and an amine.

14. The process of claim 1, wherein the catalyst is selected from the group consisting of ammonium molybdate, molybdenum oxide, and molybdic acid.

15. The process of claim 1, wherein the inert solvent is selected from the group consisting of nitrobenzene, trichlorobenzene, chloronaphthalene, alkyl benzenes, alkyl naphthalenes, and kerosenes.

* * * * *

UNITED STATES PATENT AND TRADEMARK OFFICE
CERTIFICATE OF CORRECTION

PATENT NO. : 5,602,249
DATED : February 11, 1997
INVENTOR(S) : MICHICHIKA HIKOSAKA It is certified that error appears in the above-indentified patent and that said Letters Patent is hereby corrected as shown below:

Column 7, at line 25, after "hydroxyl," delete "or".

Signed and Sealed this

Fourth Day of November, 1997

Attest:

BRUCE LEHMAN

Attesting Officer

Commissioner of Patents and Trademarks